US011045306B1

(12) United States Patent
Boudjema et al.

(10) Patent No.: US 11,045,306 B1
(45) Date of Patent: Jun. 29, 2021

(54) AUTOMATED STAGING OF HAIR GRAFTS

(71) Applicant: Boudjema-Rassman Partnership, Corona Del Mar, CA (US)

(72) Inventors: Pascal Boudjema, Paris (FR); William R Rassman, Los Angeles, CA (US)

( * ) Notice: Subject to any disclaimer, the term of this patent is extended or adjusted under 35 U.S.C. 154(b) by 0 days.

(21) Appl. No.: 17/007,624

(22) Filed: Aug. 31, 2020

(51) Int. Cl.
| *A61F 2/10*  | (2006.01) |
| *A61B 17/34* | (2006.01) |
| *A61B 34/30* | (2016.01) |
| *A61B 90/00* | (2016.01) |

(52) U.S. Cl.
CPC ............ *A61F 2/10* (2013.01); *A61B 17/3468* (2013.01); *A61B 34/30* (2016.02); *A61B 90/361* (2016.02); *A61B 2217/005* (2013.01); *A61F 2240/001* (2013.01)

(58) Field of Classification Search
CPC .. A61F 2/10; A61F 2240/001; A61B 17/3468; A61B 90/361; A61B 2217/005
See application file for complete search history.

(56) References Cited

U.S. PATENT DOCUMENTS

| 5,331,472 | A  | 7/1994  | Rassman ...................... 359/894 |
| 5,827,297 | A  | 10/1998 | Boudjema ..................... 606/133 |
| 6,572,625 | B1 | 6/2003  | Rassman ....................... 606/133 |
| 8,317,804 | B1 | 11/2012 | Rassman et al. ............. 606/133 |
| 8,366,723 | B2 | 2/2013  | Rassman et al. ............. 606/133 |
| 9,259,236 | B1 | 2/2016  | Rassman et al. ............................ A61B 17/32093 |
| 9,289,286 | B1 | 3/2016  | Bernstein et al. ........ A61F 2/10 |
| 9,420,866 | B1 | 8/2016  | Rassman et al. ...... A45D 26/00 |
| 2007/0106306 | A1* | 5/2007 | Bodduluri .............. A61B 34/32 606/133 |
| 2007/0179381 | A1* | 8/2007 | Johansson ............ G01N 21/274 600/476 |
| 2008/0051816 | A1 | 2/2008 | Pak et al. ....................... 606/187 |
| 2008/0167674 | A1 | 7/2008 | Bodduluri et al. ........... 606/187 |

(Continued)

FOREIGN PATENT DOCUMENTS

| WO | WO/2009/123635 | 10/2009 |
| WO | WO/2012/136904 | 10/2012 |
| WO | WO2015/061433  | 4/2015  |

OTHER PUBLICATIONS

U.S. Appl. No. 16/827,137, filed Mar. 23, 2020.

*Primary Examiner* — Richard G Louis
(74) *Attorney, Agent, or Firm* — Venable LLP (57) ABSTRACT

Method and apparatus for automated staging of hair grafts using a camera for capturing one or more images of a staging area constructed for holding the hair grafts, and a controllable robotic arm having an aspiration tip mounted at a tool end thereof. An image captured by the camera is processed to identify a position of a hair graft in the image, and subsequent to distinguishing between a base end and a hair end of the hair graft in the image, an aspiration point is defined based at least in part on position of either or both of the base end and the hair end. The robotic arm is controlled to move the aspiration tip to the aspiration point, for aspiration of the hair graft into the aspiration tip. The aspirated graft may then be dispensed to a holding cartridge, sorted by number of hair grafts, or may be aspirated directly from the aspiration tip to a loading position in a hair implantation device, or to a loading position in a helper device for subsequent loading of the hair graft to a hair implantation device.

28 Claims, 10 Drawing Sheets

(56) References Cited

U.S. PATENT DOCUMENTS

| | | |
|---|---|---|
| 2008/0177287 A1 | 7/2008 | Rassman et al. ............. 606/133 |
| 2009/0012536 A1 | 1/2009 | Rassman et al. ............. 606/133 |
| 2016/0235441 A1 | 8/2016 | Parkin ................ A61B 17/3468 |

\* cited by examiner

AUTOMATED STAGING OF HAIR GRAFTS

BACKGROUND

Field

The disclosure herein describes automated staging of hair grafts in preparation for implantation in the scalp of a patient.

Related Art

Hair restoration through transplantation of follicular units is an involved and time-consuming process. Individual hair grafts are harvested from a donor region in the patient's scalp, in a process that results in follicular units, each having 1-3 (or more) hairs. For example, the grafts might be harvested through follicular unit extraction or strip harvested followed by dissection of individual grafts. The grafts/follicular units are small and sized differently, mainly in diameter, in dependence on the number of hairs in the graft. Typical sizes are 5-6 mm in length by ~1 mm in width, from which on the cutaneous/upper end 1-3 hairs emerge, with the hair(s) being cut pre-surgery to a length of ~1-3 mm.

The grafts are then sorted by the number of hairs they contain: F1 for singles, F2 for two hairs and F3 and so on for 3 hairs. The number of hairs is important since the transplant surgeon will tend to implant F1s at the hairline whereas F2s, F3 s, etc. are commonly implanted in the mid-scalp and crown, so as to produce a more natural appearing aesthetic result. The sorted grafts are then individually loaded into an implantation device that typically contains only one single graft. An incision is made at an implantation site in the patient's scalp, for receipt of a single graft, and the graft is then implanted by use of the implantation device into the incision.

A typical restoration procedure might require about 2000 grafts and often involves more. A significant amount of time is consumed by the sorting of the grafts and the loading of the implantation device.

SUMMARY

Described herein are method and apparatus for automated staging of hair grafts using a camera for capturing one or more images of a staging area constructed for holding the hair grafts, and a controllable robotic arm having an aspiration tip mounted at a tool end thereof. An image captured by the camera is processed to identify a position of a hair graft in the image, and subsequent to distinguishing between a base end and a hair end of the hair graft in the image, an aspiration point is defined based at least in part on position of either or both of the base end and the hair end. The robotic arm is controlled to move the aspiration tip to the aspiration point, for aspiration of the hair graft into the aspiration tip.

The hair grafts may be held in a hydration solution at the staging area, such as in a shallow tray or on a gauze mat impregnated with a hydration solution. The staging area may be backlighted for improved contrast and detection of the grafts. Likewise, image processing to identify the grafts may include contrast enhancement.

The aspiration point may be defined as offset axially from the base end of the hair graft along an axis defined between the hair end and the base end of the hair graft, so as to ensure successful aspiration of the graft in the desired orientation while also not disturbing the position of the graft when moving the aspiration tip adjacent the graft.

After aspiration of the hair graft into the aspiration tip, the aspirated graft may be transported for temporary pre-implantation storage in a tray-like cartridge having plural wells for receipt of a respective plurality of stored grafts. In this aspect, the robotic arm is moved to a position adjacent one of the plural storage wells formed in the cartridge, and the aspirated hair graft is dispensed into the storage well. There may also be a determination of the location of a next empty storage well for dispensing the aspirated hair graft into the next empty storage well. There may be plural cartridges or cartridge sections on a single cartridge, coupled with a determination of the number of hairs in the hair graft, wherein the robotic arm is moved to one of the plural different cartridges (or cartridge sections) corresponding to the number of hairs in the hair graft.

The aspirated hair graft may be aspirated directly from the aspiration tip to a loading position in a hair implantation device, or to a loading position in a helper device for subsequent loading of the hair graft to a hair implantation device. In this regard, it may be possible for the surgeon to issue an instruction for aspiration of a hair graft having a specified number of hairs, in which case the captured image is processed to identify the position of a hair graft having the specified number of hairs.

Further objectives and advantages will become apparent from a consideration of the description, drawings, and examples.

DETAILED DESCRIPTION

Figure 1:
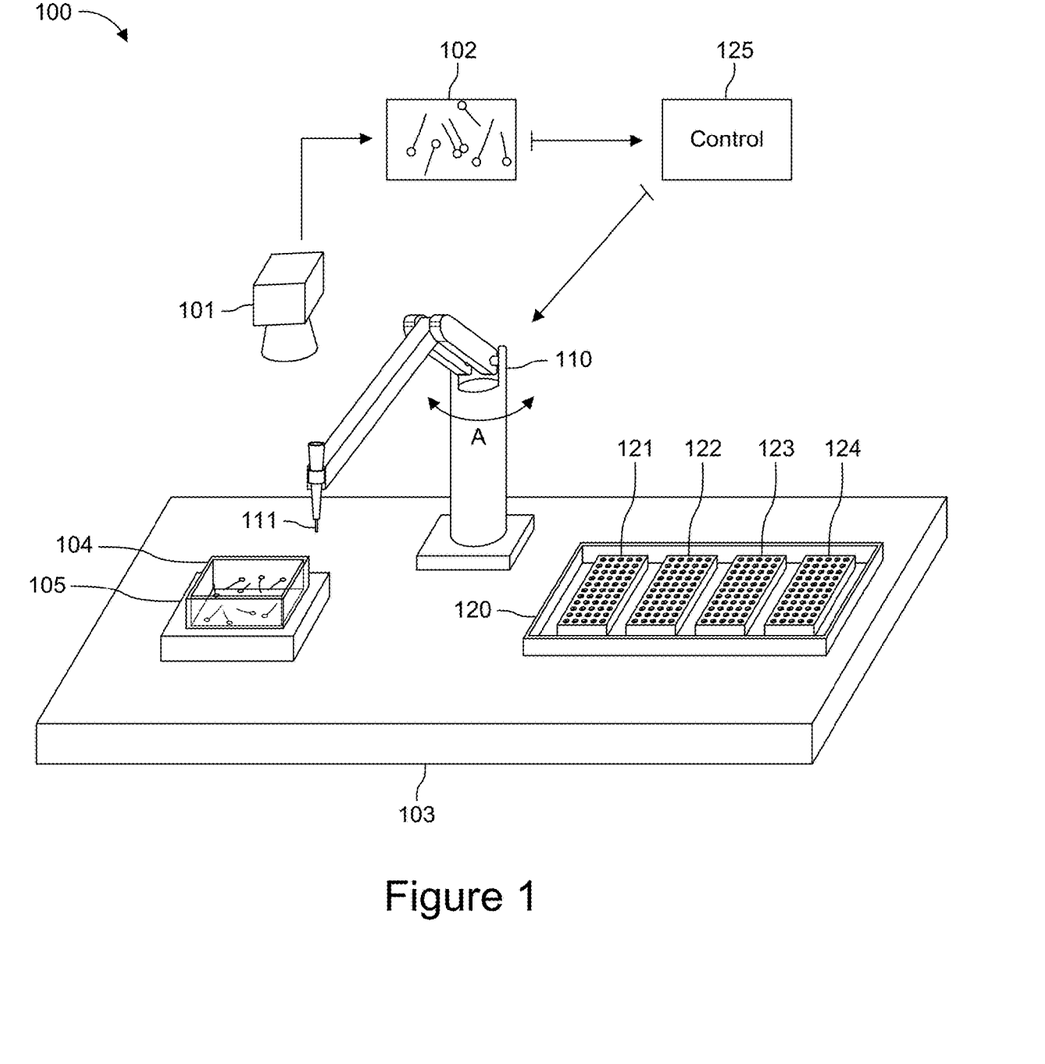
FIG. 1 is a view showing one embodiment of a staging apparatus for transporting hair grafts from a hydration solution to multiple tray-like cartridges each holding plural grafts.

FIG. 1 is a view showing one embodiment of a staging apparatus 100 for transporting hair grafts from a hydration solution to multiple tray-like cartridges each holding plural grafts in a respective plurality of storage wells. Apparatus 100 includes camera 101 for capturing one or more images 102 of staging area 103 constructed for holding multiple hair grafts in a hydration solution. The hair grafts have been harvested from a donor region on the patient's scalp as described hereinabove, and are held without any deliberate organization (i.e., held randomly positioned) in the staging area.

In this embodiment, the staging area 103 includes a shallow container 104 holding the hair grafts in hydration. A shallow container is preferable as it tends to align all hair grafts horizontally, thus permitting control of position to two axes only (X-Y axes) and not requiring a determination of vertical position of the hair graft in the hydration solution (in the Z axis), as well as control to different positions of the individual hair grafts in the Z axis. In alternate embodiments, the hair grafts can be held on a gauze mat impregnated with a hydration solution, which also permits control of position in two axes only. Container 104 may be circular or rectangular in shape, for example a Pyrex dish or other material with a homogeneous background, about 15 cm long, 10 cm wide and 4 cm high, or a plate type device measuring about 2-3 inches by 4-6 inches square with a height of approximately 1 cm. Even if the container is not shallow, the hair grafts have a density such that if they are left in a physiologic solution, they tend to position themselves spontaneously near or at the bottom of the container and remain immobile provided the physiologic liquid is not stirred. When placed in a container or on a gauze immersed in a physiologic solution, the grafts are often organized by orienting them in a uniform position, all with the poles of the grafts organized in the same direction. The grafts can be further organized into groupings that reflect the number of hairs in each graft. In general, however, the hair grafts will be disorganized. Naturally, use of a shallow container or a gauze mat are a non-limiting examples and other arrangements can be used inclusive of arrangements that require control of position in the third axis.

In this embodiment, the staging area is backlighted by backlight 105, for improved contrast and detection of the hair grafts.

A three-axis robotic arm 110 is arranged adjacent the staging area in a pick-and-place configuration indicated generally by arrow A. Other embodiments might use a six-axis robotic arm. Aspiration tip 111 in the form of a hollow needle is mounted at the tool end of the robotic arm and is connected by tubing to an unshown vacuum source.

Four tray-like cartridges, each constructed to hold plural hair grafts, are positioned in a tray 120 holding hydration solution. Each cartridge is designated to hold hair grafts having different numbers of hairs. Thus, cartridge 121 designated to hold F1s, cartridge 122 is designated to hold F2s, cartridge 123 is designated to hold F3s, and cartridge 124 is designated to hold F4s (and higher). While this embodiment uses multiple cartridges for this purpose, alternative embodiments can be envisioned, for example, a cartridge having different sections designated for hair grafts with different numbers of hairs.

Controller 125 is a software-based controller having a processor and a memory for storing data as well as process steps. Under control of controller 125, an image such as image 102 is captured by camera 101 and is processed to identify a position of a hair graft in the image. Controller 125 distinguishes between a base end and a hair end of the hair graft in the image, and defines an aspiration point based at least in part on position of either or both of the base end and the hair end. Controller 125 controls robotic arm 110 to move aspiration tip 111 to the aspiration point, for aspiration of the hair graft into the aspiration tip. Based on a determination of the number of hairs in the hair graft, controller 125 moves the robotic arm to a corresponding one of cartridges 121-124 and dispenses the aspirated hair graft to one of plural wells in the cartridge.

The cartridges are designed to work with another system, which may be a manual system but which may also be a robotic system, which will move from well to well, one at a time, to grasp the graft with suction and then the graft will travel through tubing into an implantation device or to a helper device from which the implantation device is loaded. One purpose of the cartridge is to hold the graft in a hydrated manner until, later, it will be moved to either a hand-held implanter or a robotic implanter.

Figure 2:
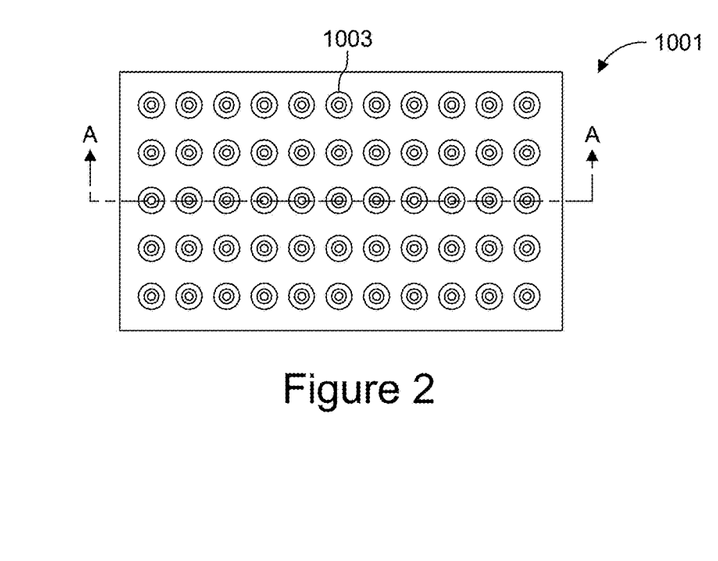
FIGS. 2, 2A, 2B and 2C are views showing details of an example cartridge.
Figure 2A:
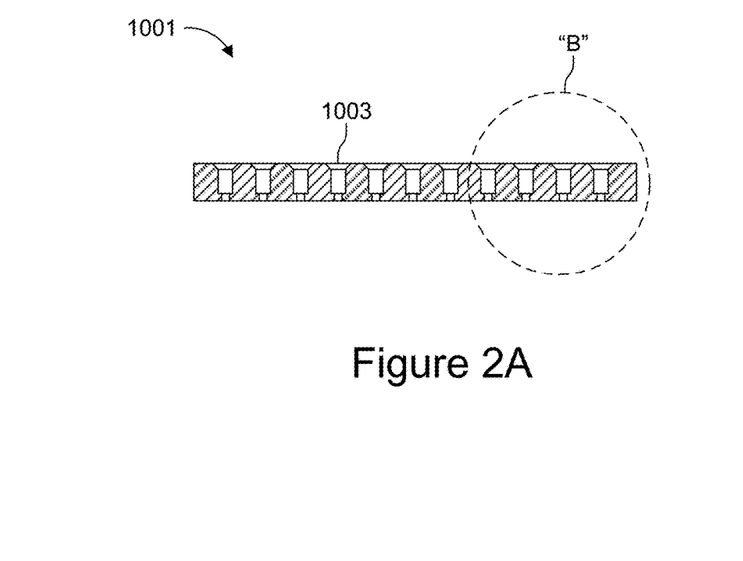
Figure 2B:
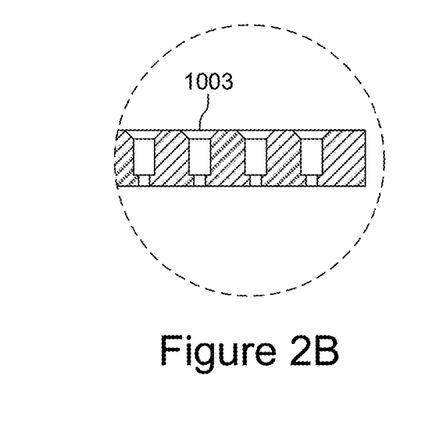
Figure 2C:
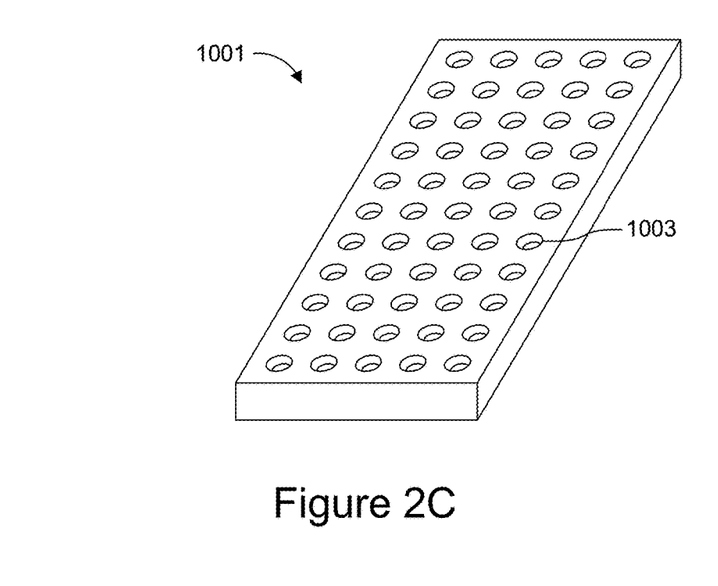

FIGS. 2, 2A, 2B and 2C are views of one of the tray-like cartridges 121-124 according to an example embodiment, here designated as 1001. FIG. 2 is a top view of cartridge 1001 showing a top view of several hair graft storage wells 1003. Each of the hair graft storage wells is configured to house one hair graft that is to be transported to an implantation device for implanting hair grafts. In some embodiments, each of the hair graft storage wells may be configured to house more than one hair graft. The hair graft storage wells 1003 are further configured to ensure that the hair grafts are properly oriented with the hair end up and the base end down. FIG. 2A is a sectional view of the hair graft storage tray of FIG. 2 along the A-A axis. FIG. 2B is a zoomed-in view of the "B" region indicated in FIG. 2A and FIG. 2C is a perspective view of the hair graft storage tray.

Figure 3:
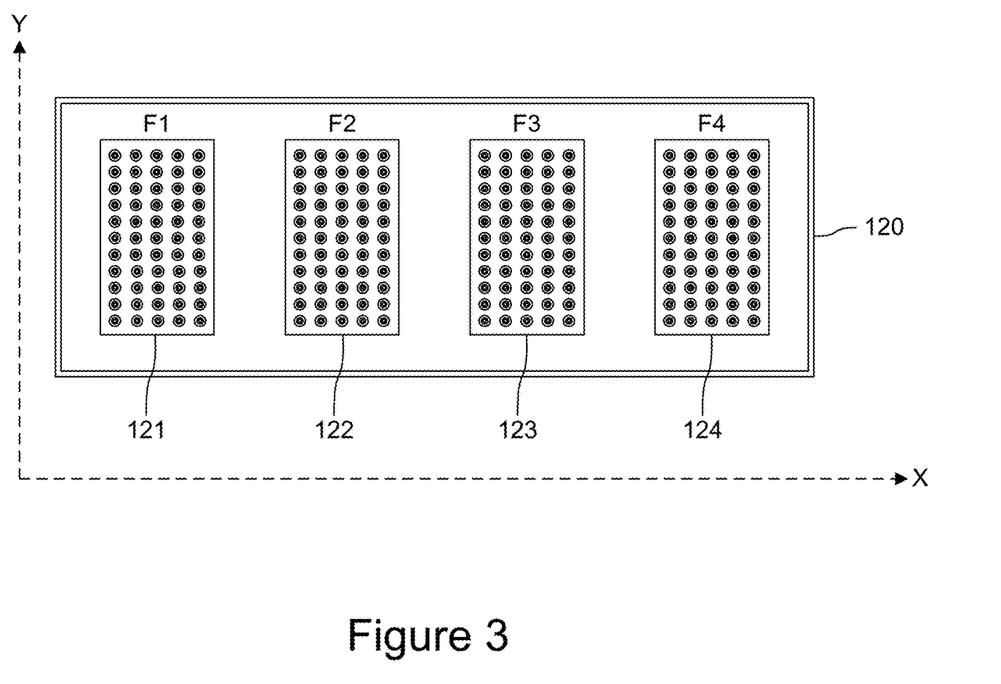
FIG. 3 is a view for explaining X-Y positioning for the cartridges.

FIG. 3 is a view for explaining X-Y positioning for the cartridges 121-124. In this embodiment, tray 120 includes positioning means, such as recessed surfaces or guide rails, that permit precise positioning of cartridges 121-124 in X and Y axes of a horizontal plane.

Figure 4:
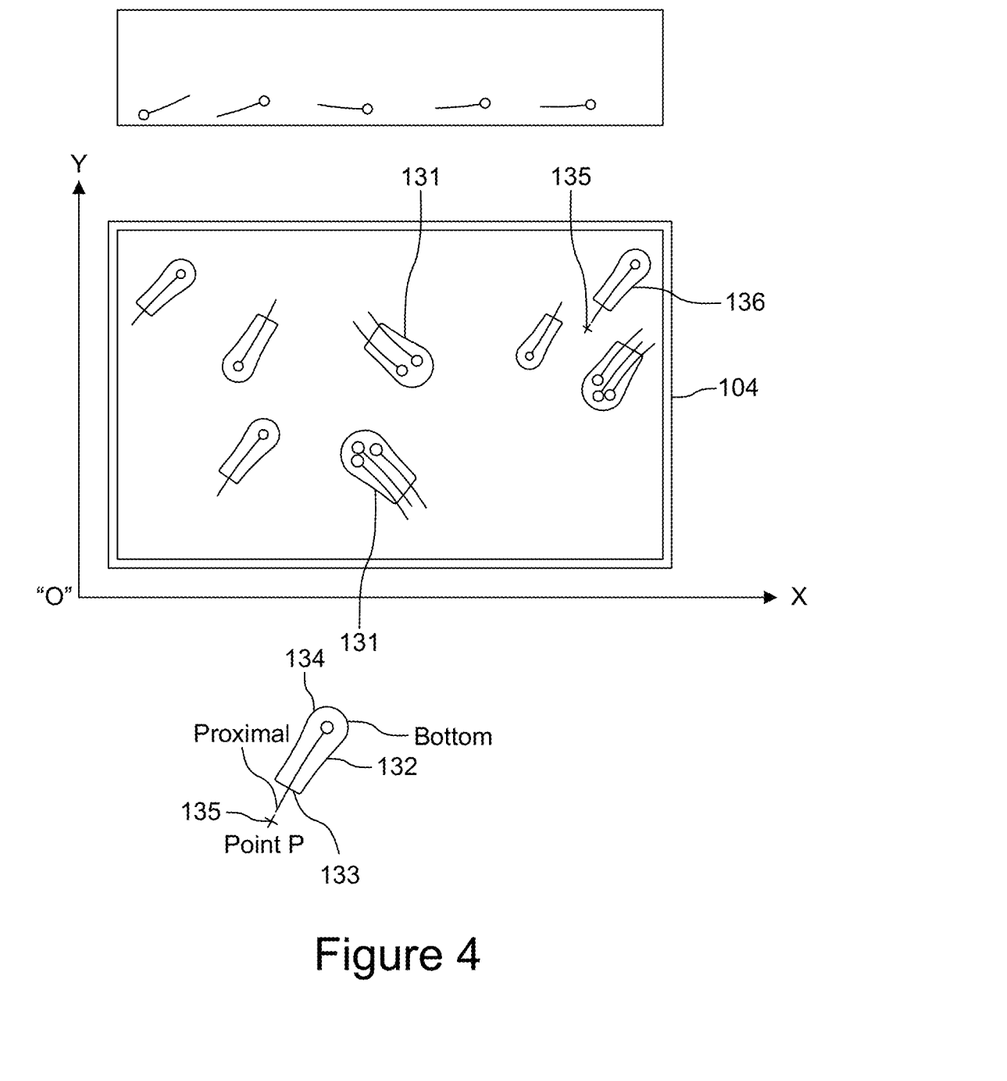
FIG. 4 is a view for explaining X-Y positioning of hair grafts in the hydration solution.

FIG. 4 is a view for explaining X-Y positioning of hair grafts in hydration solution in tray 104, relative to origin "0". As seen in this figure, hair grafts 131 lie in disorganized orientation in tray 105, randomly, with mixed ones of F1s, F2s and so forth. As indicated at 132, each graft has a proximal end 133 (i.e., the hair/upper/cuteneous end) and a distal end 134 (i.e., the bottom/base end). For any one hair graft, controller 125 will define an aspiration point 135 offset axially from the base end of the hair graft along an axis defined between the hair end and the base end of the hair graft, so as to be near enough to the hair graft to ensure successful aspiration of the graft in the desired orientation while also far enough from the hair graft so as not to disturb the position of the graft when moving the aspiration tip adjacent the graft.

Figure 5:
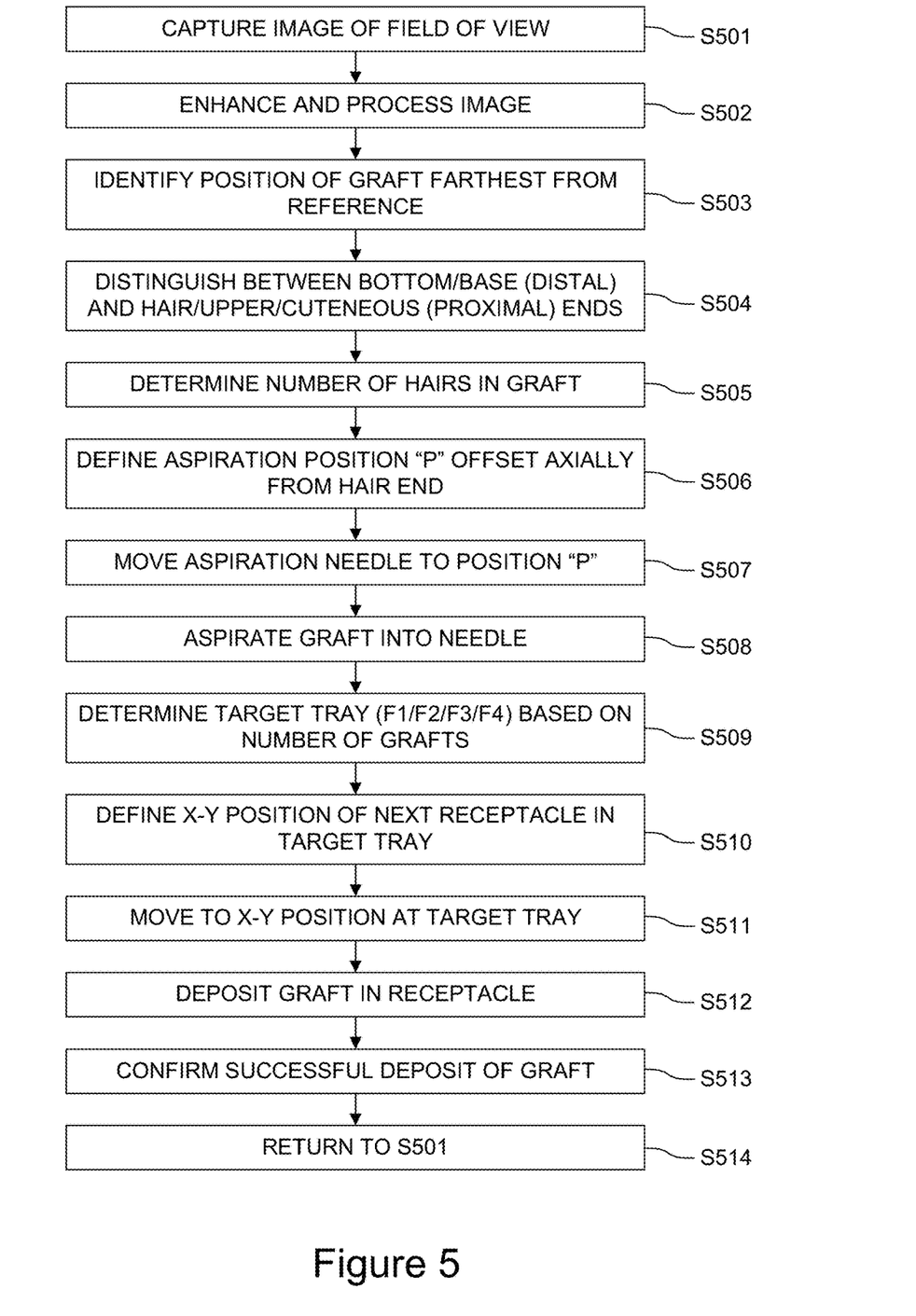
FIG. 5 is a flowchart for explaining one example of an aspiration sequence.

FIG. 5 is a flowchart for explaining one example of an aspiration sequence. In step S501 camera 101 captures an image 102 of the field of view.

Figure 6:
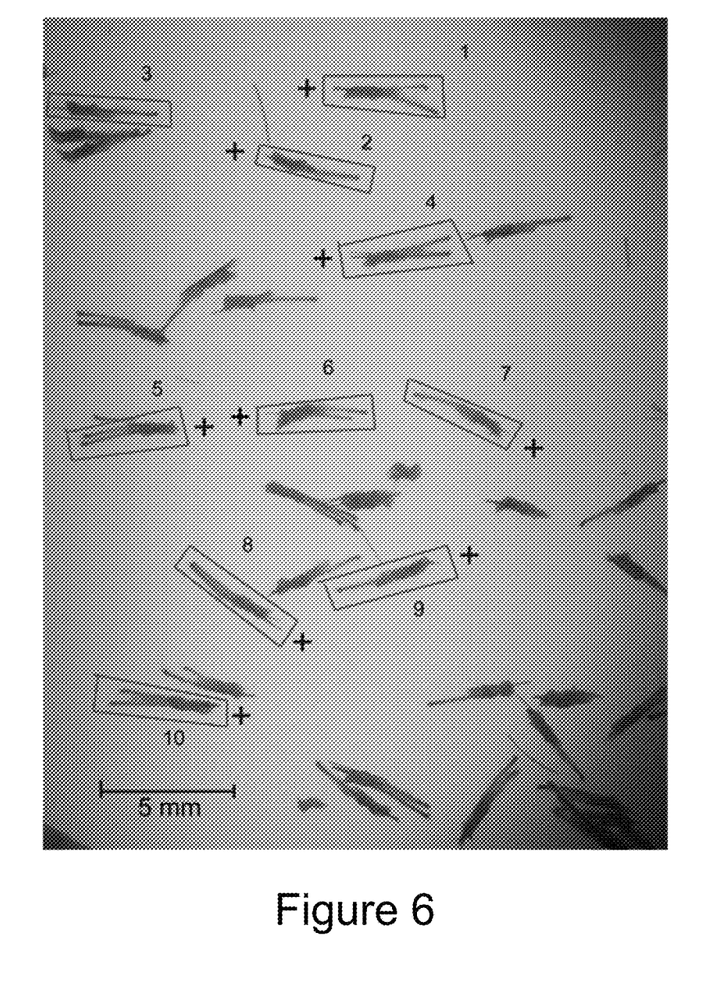
FIG. 6 is an example of a captured image of hair grafts in the hydration solution.

FIG. 6 is an example of a captured image of hair grafts according to step S501, although FIG. 6 also depicts the results of some of the image processing by which the position and orientation of the hair grafts is determined. As seen in FIG. 6, the grafts placed in a transparent pyrex container are arranged randomly on a backlit plate. Exploitable hair grafts are framed in rough rectangles. A cross pattern ("+") corresponds to an aspiration point where the aspiration tip 111 must be positioned. It is observed that the shape of the grafts is variable. For example, graft #1 has at its upper pole a single small hair while at the opposite pole there are two divergent roots.

In step S502, the captured image is enhanced and processed for locating the position and orientation of the hair grafts.

Figure 7:
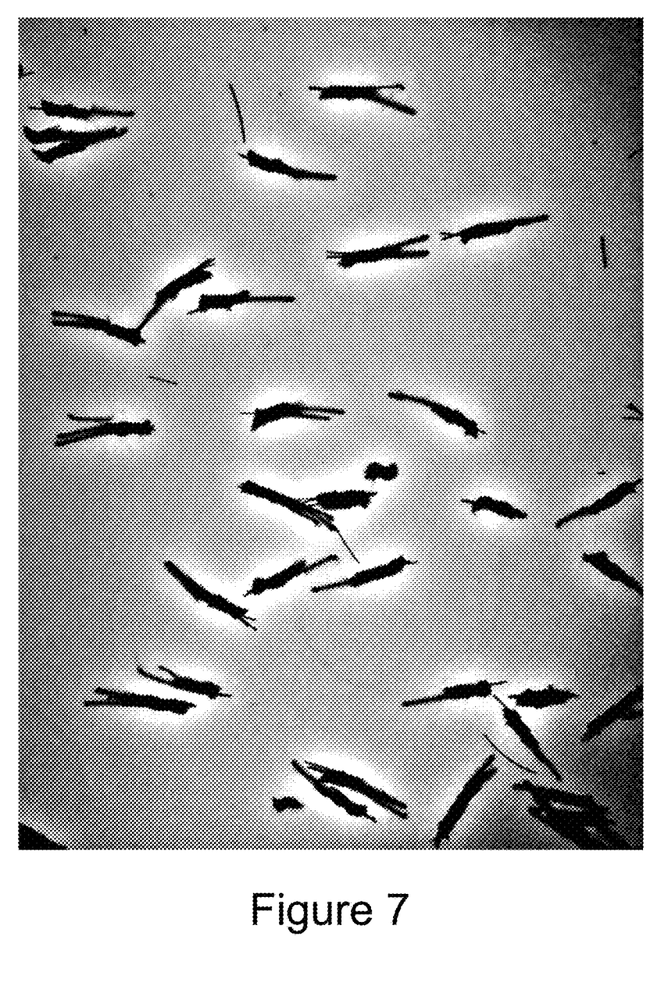
FIG. 7 is an example of image enhancement of the captured image.

FIG. 7 is an example of image enhancement of the captured image according to step S502. In this example, image enhancement increases contrast of the image, which, coupled with backlighting of staging area 103, provides for increased ability to identify the position and orientation of hair grafts.

In step S503, controller 125 identifies the position of the graft farthest from reference point "O" (see FIG. 4). Referring to FIG. 4, hair graft 136 is identified as it is farthest from reference point "O".

In step S504, controller 125 distinguishes between the bottom/base (distal) end and the hair/upper/cutaneous (proximal) end. In step S505, the controller determines the number of hairs in graft 136, and in step S506, controller 125 defines an aspiration position ("P" in FIG. 4 and marked by crosses "+" in FIG. 6) offset axially from the hair end of the hair graft along an axis defined by the hair and base ends of the graft.

The axial offset by which the open hole of the aspiration needle 111 is placed from the hair end of the hair graft is typically between 1 to 3 mm from the cutaneous end of the graft. In some embodiments, the axial offset may depend also on the position and the shape of the tip of the aspiration needle 111 on the XY plan. In this embodiment, the tip of the aspiration needle on the XY plane is square, and it is fixed vertically to the robot arm on the Z axis. In other embodiments, the tip of the aspiration needle is beveled such as a 45 degree bevel, and although it is fixed vertically to the robot arm on the Z axis, it is also mounted for robotically-controlled rotation around the Z axis, so as to present a beveled open tip of the needle facing to the graft. In that case, the robot arm further includes a step motor to rotate the needle on a Theta angle +−360°. The robot arm moves on 4 axis: XYZ and Theta to rotate the needle on itself around the Z axis.

In step S507, controller 125 controls robotic arm 110 to move aspiration needle 111 to the defined aspiration position, and in step S508 the hair graft is aspirated into needle 111.

In step S509, based on the number of hairs in the graft as determined by step S505, controller 125 determines the target one of cartridges 121-124 (i.e., F1/F2/F3/F4). Controller 125 includes a memory which stores the X-Y location of all wells of all cartridges, and which also stores a list of wells already in use. Thus, in step S510, controller 125 defines the X-Y position of next unused well in the targeted one of cartridges 121-124 tray In step S511, controller 125 move robotic arm 110 so that aspiration tip 111 is moved to the X-Y position of the well in the targeted cartridge.

In step S512, the aspirated hair graft is dispensed into the designated well.

Figure 8:
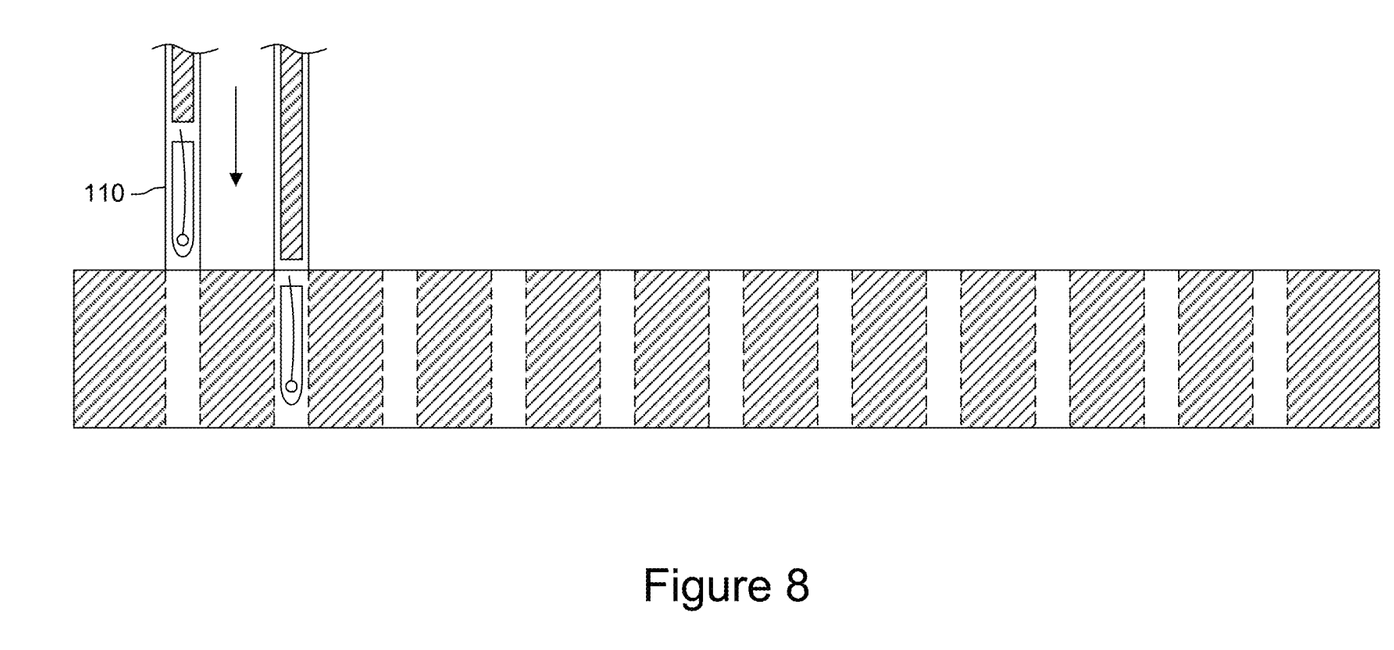
FIG. 8 is a view showing an example of an aspirated hair graft being dispensed into a well of a cartridge.

FIG. 8 is a view showing an example of an aspirated hair graft being dispensed into the well in the targeted cartridge. In this embodiment, the well is completely cylindrical, without a taper at the bottom or the cross-sectional "Y"-shape of FIG. 2B. This shape allows (for example) to place the filled cartridge on an implantation device that accepts such cartridges (for example used actually by the Artas Robot) where the grafts would be pushed into the scalp by a rod or plunger in the same direction (without narrowing at the bottom of the well).

As seen in FIG. 8, robotic arm 110 with aspiration tip 111 takes an X-Y position above the targeted well and is moved downward in the Z direction toward the rim of the well. The aspirated graft inside the needle is dispensed into the well such as by being flushed into the well by a piston or a rod, or by means of positive pressure.

In step S513, an unshown vision system is used to confirm successful dispensing of the hair graft into the well. The memory of controller 125 is updated accordingly, to mark the well as "used". Flow thereafter returns to step S501 (step S514).

Typically, a new image is captured after each aspiration, to account for movement of the grafts. If a bath is used for storage in container 104, it is possible to mix or agitate the physiological liquid by mechanical means to separate grafts agglomerated between them, and to carry out a new image acquisition process. It is also possible to use a vibrating plate placed under the container 104 to separate the intersecting or agglomerated grafts. It should be understood that at the end of each individual retrieval cycle, when a bath of physiologic solution is used, suction of the graft may cause a displacement of neighboring graft within the bath. It is therefore preferable to redo an analysis and a new acquisition of the coordinates (X-Y) of the exploitable grafts at the end of each cycle.

In order to reduce the probability of agglomeration or the overlapping of the grafts, it may be preferable to reduce the quantity of grafts placed in the container (for example a reduction from 150 grafts to 50 grafts placed on a surface of 150 cm^2 in a physiologic bath).

Regarding the lighting of the detection zone, there may be direct lighting by LEDs or filters of different colors, possibly associated with the backlight to improve the definition and the details of the graft samples.

Figure 9:
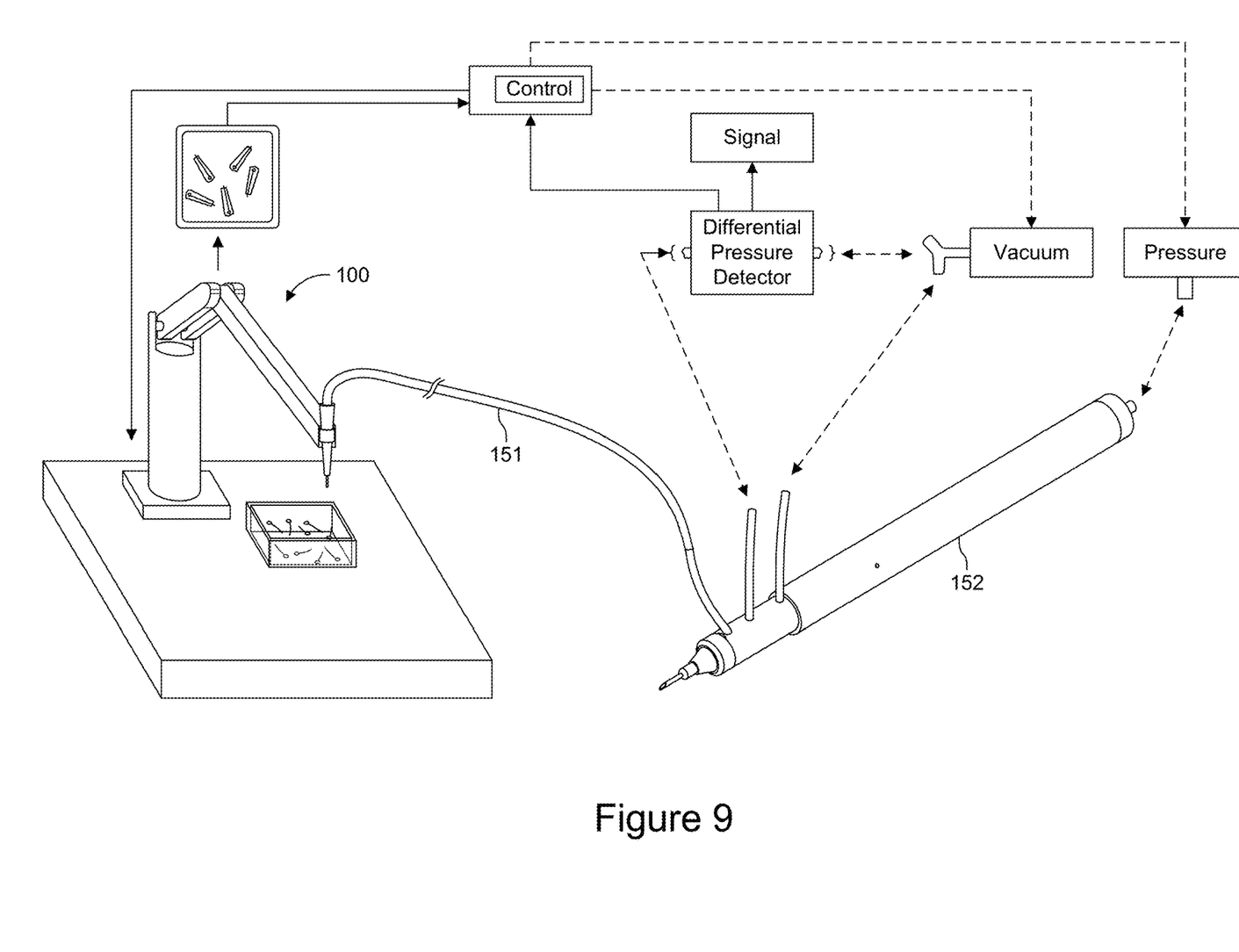
FIG. 9 is view showing an example of aspiration of a hair graft directly from the hydration solution to a loading position in a hair implantation device.

FIG. 9 is view showing an example of aspiration of a hair graft directly from the hydration solution, through tubing 151, to a loading position in hair implantation device 152. An example of a suitable device for hair implantation device 152 is found in U.S. patent application Ser. No. 16/827,137 filed Mar. 23, 2020, "Vacuum Driven Implantation Device", the entire contents of which are incorporated by reference herein.

Figure 10:
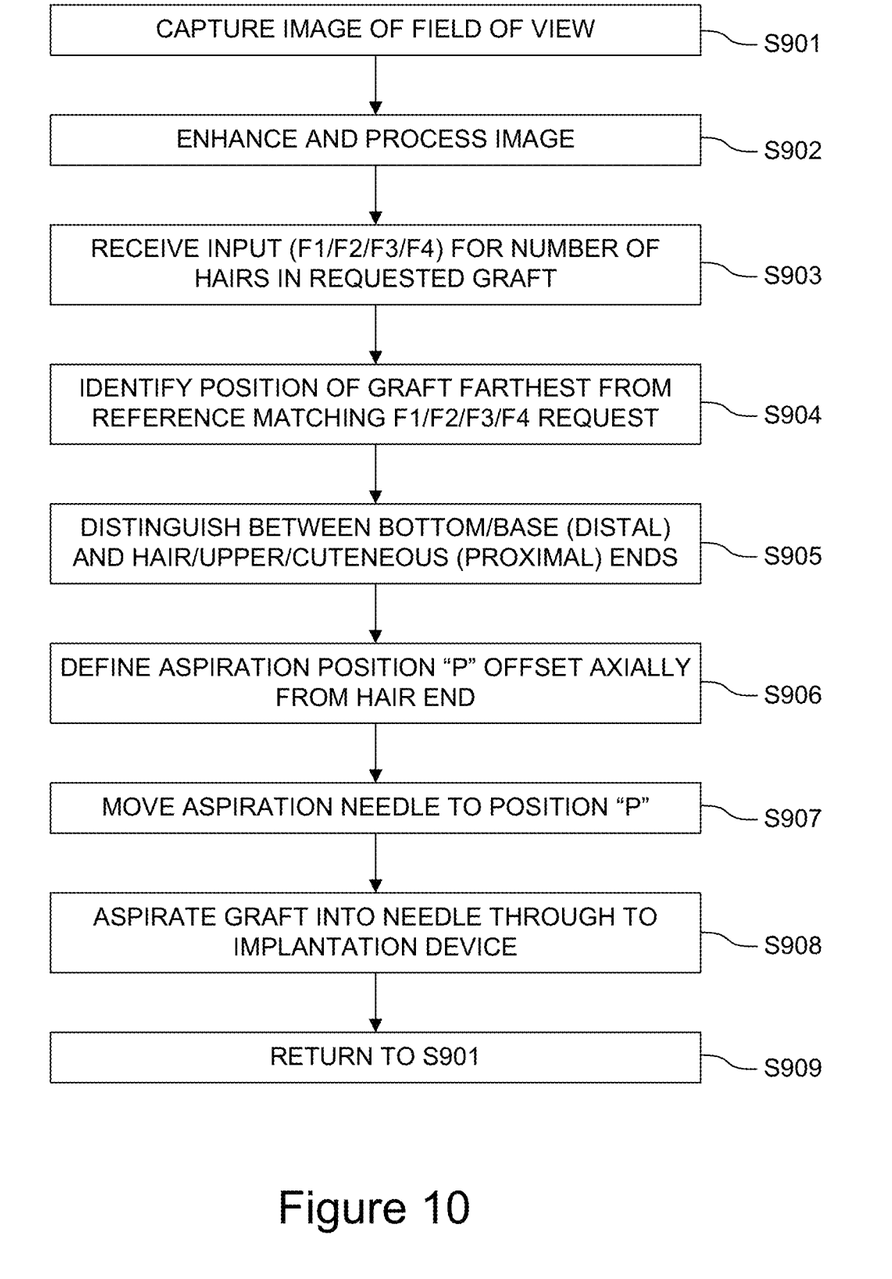
FIG. 10 is a flowchart for explaining another example of an aspiration sequence.

FIG. 10 is a flowchart for explaining an example of an aspiration sequence applicable to FIG. 9.

In step S901, camera 101 captures an image of the field of view, and in step S902, controller 125 enhances and otherwise processes the image, as in FIG. 5.

In step S903, the surgeon issues an instruction for the type of graft (F1/F2/F3/F4) desired for the current implantation site, and this instruction is received by controller 125. In step S904, controller 125 identifies the position of a hair graft farthest from reference point "O" that also matches the requested type of graft (F1/F2/F3/F4). Thereafter, in like manner to FIG. 5, controller 125 distinguishes between the bottom/base (distal) end and the hair/upper/cuteneous (proximal) end (step S905), defines aspiration position "P" offset axially from hair end (step S906), and moves aspiration needle to position "P" (step S907).

In step S908, the hair graft is aspirated directly from the hydration solution, through tubing 151, to a loading position in hair implantation device 152. Flow thereafter returns to step S901 where, like in FIG. 5, another image is typically captured prior to a further aspiration of a hair graft.

Figure 11:
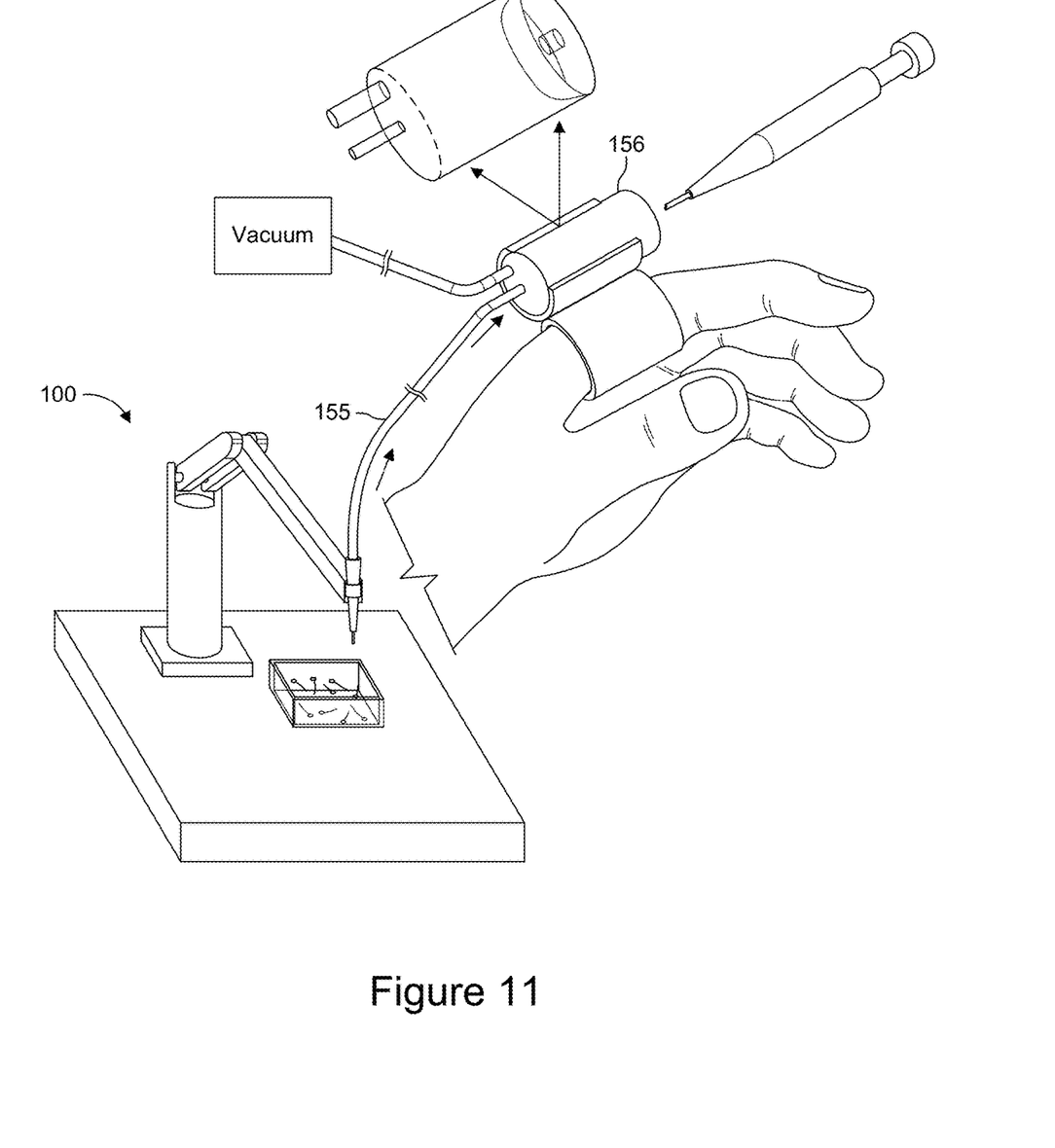
FIG. 11 is is view showing an example of aspiration of a hair graft directly from the hydration solution to a loading position in a helper device for subsequent loading of the hair graft to a hair implantation device

FIG. 11 is a view showing an example of aspiration of a hair graft directly from the hydration solution, through tubing 155, to a loading position in a helper device 156 for subsequent loading of the hair graft to a hair implantation device. An example of a suitable device for helper device 156 is found in WO 2020/065144, published Apr. 2, 2020, "Device for Loading Hair Grafts Into an Instrument for Graft Implantation". The aspiration sequence of FIG. 10 (steps S901 etc.) is applicable also to the arrangement depicted in FIG. 11.

It will be understood from the foregoing that autonomous staging of hair grafts is achievable by using a robotic arm driven by an interface using a machine vision camera that is controlled by a software controller. The difficulties addressed by the arrangements described herein include:

1. At the level of the graft tissue sample, it is is frequently important to identify the graft's upper and lower pole and the number of hairs in each graft.
2. Considering the variations in shape and size of the grafts, it is frequently necessary to define the common points between them as well as their differences (inclusion and exclusion)
3. Identifying the proximal end from the distal end
4. Identifying the number of hairs in each graft
5. Identifying the position of the aspiration tip to suck up the graft
6. Being sure that the correct number of hairs for each graft is directed to either the (a) surgeon's instrument or (b) a cartridge which will store the grafts based upon the number of hairs in each graft in specified locations.
7. One or more cartridges may be used for the storage of the grafts, each cartridge containing grafts with a different number of hairs in each graft Furthermore:
1. Reliable localization of the upper pole of the graft with good camera resolution is obtained
2. Allowing to visualize the number of hairs in each graft and route them to their destination to either (a) the surgeon's instrument on demand, one by one, or (b) a storage cartridge. It is frequently important for the software to organize an orderly placement of the grafts into either a defined physical location within a single cartridge or into a cartridge for single hair grafts only (F1s), a cartridge for 2 hairs grafts only (F2s), or a cartridge for three or more hair grafts (F3s etc.). Appropriate mapping software and memory of controller 125 allows for a reliable retrievable system for graft removal from the cartridge with a surgical robot, slot by slot, traveling to either a hand-held implanter or a robotic held implanter. In this way, the movement of 1,2 or 3 or more hair grafts can meet the surgeon's requirement for implantation at any instant point in time.
3. The positioning of the aspiration tip/suction tubing on only a single graft
4. Eliminate overlapping of grafts to avoid aspirating 2 grafts at the same time (exclusion)

The embodiments illustrated and discussed in this specification are intended only to teach those skilled in the art how to make and use the disclosure herein. In describing embodiments of the disclosure herein, specific terminology is employed for the sake of clarity. However, the disclosure herein is not intended to be limited to the specific terminology so selected. The above-described embodiments of the disclosure herein may be modified or varied, without departing from the disclosure herein, as appreciated by those skilled in the art in light of the above teachings. It is therefore to be understood that, within the scope of the claims and their equivalents, the disclosure herein may be practiced otherwise than as specifically described.

The invention claimed is:

1. Apparatus for staging of hair grafts, comprising:
a staging area holding hair grafts in a hydration solution;
a camera for capturing one or more images of hair grafts at the staging area;
a controllable robotic arm having an aspiration tip mounted at a tool end thereof; and
a control unit constructed to:
process an image captured by the camera to identify a position of a hair graft in the image;
distinguish between a base end and a hair end of the hair graft in the image;
define an aspiration point based at least in part on position of either or both of the base end and the hair end;
control the robotic arm to move the aspiration tip to the aspiration point, for aspiration of the hair graft into the aspiration tip.

2. The apparatus according to claim 1, wherein the aspiration point is offset axially from the base end of the hair graft along an axis defined between the hair end and the base end of the hair graft.

3. The apparatus according to claim 2, wherein the aspiration tip is beveled and is controlled for rotational movement around a longitudinal axis of the aspiration tip so as to present a beveled open tip to the hair graft for aspiration of the hair graft.

4. The apparatus according to claim 1, wherein the staging area is backlighted.

5. The apparatus according to claim 1, wherein the hair grafts are held in a backlighted shallow tray in the hydration solution at the staging area.

6. The apparatus according to claim 1, wherein the hair grafts are held on a gauze mat impregnated with the hydration solution at the staging area.

7. The apparatus according to claim 1, wherein processing of the captured image to identify position of the graft includes contrast enhancement of the captured image.

8. The apparatus according to claim 1, wherein after aspiration of the hair graft into the aspiration tip, the control unit is further constructed to move the robotic arm to a position adjacent one of plural storage wells formed in a cartridge, and to dispense the aspirated hair graft into said one storage well.

9. The apparatus according to claim 8, wherein the control unit is further constructed to determine the location of a next empty storage well and to dispense the aspirated hair graft into the next empty storage well.

10. The apparatus according to claim 8, wherein the control unit is further constructed to determine the number of hairs in the hair graft and to move the robotic arm to one of plural different cartridges corresponding to the number of hairs in the hair graft.

11. The apparatus according to claim 1, wherein the control unit is further constructed to receive an instruction for aspiration of a hair graft having a specified number of hairs, and wherein the captured image is processed to identify the position of a hair graft having the specified number of hairs.

12. The apparatus according to claim 1, further comprising tubing to connect the aspiration tip to a hair implantation device, wherein the aspirated hair graft is aspirated to a loading position in the hair implantation device.

13. The apparatus according to claim 1, further comprising tubing to connect the aspiration tip to a helper device, wherein the aspirated hair graft is aspirated to a loading position in the helper device for subsequent loading of the hair graft to a hair implantation device.

14. The apparatus according to claim 1, wherein the grafts held at the staging area are disorganized with base ends and hair ends of the grafts in non-aligned arrangements.

15. A method for staging of hair grafts, comprising:
capturing one or more images of a staging area constructed for holding hair grafts, wherein the hair grafts are held in a hydration solution at the staging area;

processing a captured image to identify a position of a hair graft in the image;

distinguishing between a base end and a hair end of the hair graft in the image;

defining an aspiration point based at least in part on position of either or both of the base end and the hair end;

controlling a robotic arm to move an aspiration tip mounted thereon to the aspiration point, for aspiration of the hair graft into the aspiration tip.

16. The method according to claim 15, wherein the aspiration point is offset axially from the base end of the hair graft along an axis defined between the hair end and the base end of the hair graft.

17. The method according to claim 16, wherein the aspiration tip is beveled and is mounted for rotational movement around a longitudinal axis of the aspiration tip, and further comprising rotating the aspiration tip so as to present a beveled open tip to the hair graft for aspiration of the hair graft.

18. The method according to claim 15, wherein the staging area is backlighted.

19. The method according to claim 15, wherein the hair grafts are held in a backlighted shallow tray in the hydration solution at the staging area.

20. The method according to claim 15, wherein the hair grafts are held on a gauze mat impregnated with the hydration solution at the staging area.

21. The method according to claim 15, wherein processing of the captured image to identify position of the graft includes contrast enhancement of the captured image.

22. The method according to claim 15, wherein after aspiration of the hair graft into the aspiration tip, further comprising moving the robotic arm to a position adjacent one of plural storage wells formed in a cartridge, and dispensing the aspirated hair graft into said one storage well.

23. The method according to claim 22, further comprising determining the location of a next empty storage well and dispensing the aspirated hair graft into the next empty storage well.

24. The method according to claim 22, further comprising determining the number of hairs in the hair graft and moving the robotic arm to one of plural different cartridges corresponding to the number of hairs in the hair graft.

25. The method according to claim 15, further comprising receiving an instruction for aspiration of a hair graft having a specified number of hairs, and wherein the captured image is processed to identify the position of a hair graft having the specified number of hairs.

26. The method according to claim 15, further comprising aspirating the hair graft directly to a loading position in a hair implantation device.

27. The method according to claim 15, further comprising aspirating the hair graft directly to a loading position in the helper device for subsequent loading of the hair graft to a hair implantation device.

28. The method according to claim 15, wherein the grafts held at the staging area are disorganized with base ends and hair ends of the grafts in non-aligned arrangements.

* * * * *